United States Patent [19]

McCoy et al.

[11] 3,951,857

[45] Apr. 20, 1976

[54] ALKYLATION CATALYST ADDITIVE

[75] Inventors: Frederic C. McCoy, Beacon; Edward L. Cole, Fishkill, both of N.Y.

[73] Assignee: Texaco Inc., New York, N.Y.

[22] Filed: June 24, 1974

[21] Appl. No.: 482,182

Related U.S. Application Data

[62] Division of Ser. No. 413,123, Nov. 5, 1973, Pat. No. 3,865,896.

[52] U.S. Cl. .................................. 252/428; 252/436
[51] Int. Cl.² ..................... B01J 27/02; B01J 31/02
[58] Field of Search ............................ 252/428, 436

[56] References Cited
UNITED STATES PATENTS

| | | | |
|---|---|---|---|
| 2,242,845 | 5/1941 | Blount | 252/428 X |
| 2,981,772 | 4/1961 | Holzman et al. | 252/428 X |
| 3,870,765 | 3/1975 | McCoy et al. | 252/428 X |

*Primary Examiner*—Patrick P. Garvin
*Attorney, Agent, or Firm*—T. H. Whaley; C. G. Ries; Douglas H. May, Jr.

[57] ABSTRACT

NN'N'' tris (alkyl) phosphoric triamide alkylation aids of the formula

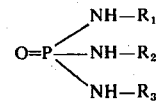

wherein $R_1$, $R_2$ and $R_3$ are selected from straight or branched chain alkyl having 10 to 24 carbon atoms each, for use in strong acid catalyzed reactions wherein alkylatable hydrocarbons are alkylated with alkylating agents. Also, alkylation processes employing such alkylation aids.

2 Claims, No Drawings

ALKYLATION CATALYST ADDITIVE

This is a division of application Ser. No. 413,123, filed Nov. 5, 1973, now U.S. Pat. No. 3,865,896, issued Feb. 11, 1975.

BACKGROUND OF THE INVENTION

The present invention relates to an improved alkylation process. In particular, this invention relates to a strong acid catalyzed reaction wherein an alkylatable hydrocarbon is alkylated with an olefin to form alkylate hydrocarbons. More particularly, the present invention relates to strong acid catalyzed alkylation of isoparaffin hydrocarbons with olefin hydrocarbons to form highly branched alkylate hydrocarbons suitable for use in the blending of gasoline.

Alkylation processes for reaction of alkylatable hydrocarbons with olefin hydrocarbons are well known and practiced widely upon a commercial basis. Commonly, an alkylatable hydrocarbon such as an isoparaffin or aromatic is reacted in the liquid phase with an olefin hydrocarbon in the presence of a heterogeneous, liquid-phase strong acid catalyst. Of particular commercial importance is the alkylation of low boiling isoparaffin hydrocarbons such as isobutane, isopentane, isohexane, etc. with low boiling olefin hydrocarbons such as propylene, butylenes, isobutylenes, etc., to form high octane alkylate hydrocarbons suitable for use as gasoline blend stocks. The reactants may not be normally liquid, consequently, superatmospheric pressures are commonly employed to maintain reactants in the liquid phase. Reaction temperatures are preferably in the range of below 0° to 150°F. Strong acid catalysts, such as sulfuric acid, fluorosulfonic acid, mixtures thereof, and hydrogen fluoride, are commonly employed in commercial processes. The catalyst used is brought into intimate contact with reactants by agitation or other mixing means. Under such reaction conditions, olefin hydrocarbons tend to react together forming polymer compounds as well as reacting with isoparaffin hydrocarbons to form the desired isoparaffin-olefin alkylation product. Such olefin polymer by-products also tend to crack in the presence of the strong acid catalyst thus forming undesirable low octane light alkylate as well as equally undesirable high molecular weight heavy alkylate compounds. Additionally, olefin polymers are difficult to separate from the strong acid catalyst and form acid-oil sludges therein. The presence of such acid-oil sludges as well as water in the strong acid catalyst decreases the strength of the strong acid catalyst. Such decrease in acid catalyst strength contributes to an increase in undesirable side reactions, such as olefin polymerization as well as decreasing the effectiveness of the acid catalyst for alkylation of isoparaffin with olefins.

Desirably, the alkylate product comprises a major portion of the highly branched isomers of the isoparaffin-olefin alkylation reaction product. For example, in the alkylation of isobutane with butene, trimethylpentanes are the desired product, and in the alkylation of isobutane with propylene, dimethylpentanes are the desired product. Low catalyst acidity due to the presence of acid-oil sludges and water contributes to production of less highly branched alkylate isomers which have lower octane values than more highly branched isomers, and consequently are of less value in gasoline blending. Additionally, cracked olefin polymers contribute substantial amounts of undesirable light and heavy alkylate compounds which have substantially lower octane values than the highly branched isoparaffin-olefin alkylation products.

It is known that surface active compounds may be employed in admixture with strong acid catalysts in an alkylation process to improve the production of highly branched isoparaffin-olefin alkylation products at the expense of olefin polymers and the resulting light and heavy alkylate compounds. Also, the use of surface active agents decreases the consumption of acid catalyst in an alkylation process. For example reference may be made to the following U.S. Patents which describe a variety of surface active compounds which may be used in alkylation processes described herein: U.S. Pat. Nos. 2,880,255; 3,551,514; 2,981,772; 3,231,633; 3,364,280; and 3,324,196. Such surface active agents, disclosed in the preceding patents, are effective for reducing the surface tension of the strong acid catalyst thereby improving contact of the catalyst with reactant hydrocarbons. It is also postulated that perhaps these surface active agents may serve to increase solubility of reactant hydrocarbons within the liquid catalyst phase. As a consequence, such surface active agents must be used with care since relatively small amounts tend to create stable emulsions of reactant hydrocarbon and acid catalyst under the conditions of agitation and mixing commonly employed in commercial alkylation reactions. Such reactant acid emulsions are difficult to break thus complicating separation of acid catalyst from hydrocarbon effluent of an alkylation process.

SUMMARY OF THE INVENTION

Now, according to the present invention, it has been discovered that alkylation of an alkylatable hydrocarbon with an olefin hydrocarbon in the liquid phase in the presence of a strong liquid acid alkylation catalyst may be substantially improved by employing from about 0.0005 to about 0.5 weight percent of a NN'N'' tris (n-alkyl) phosphoric triamide alkylation aid having the formula:

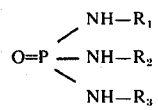

wherein $R_1$, $R_2$ and $R_3$ are selected from straight or branched chain alkyl radicals having from about 10 to 24 carbon atoms each.

By following the method of the present invention, production of desirable alkylate hydrocarbon products in an alkylation reaction is substantially increased. Also, consumption of acid catalyst within the alkylation reaction is substantially decreased. These and other advantages of the present invention will be more fully disclosed in the detailed description of the invention which follows.

DETAILED DESCRIPTION OF THE INVENTION

Surprisingly, it has been found that certain NN'N'' tris (n-alkyl) phosphoric triamides represented by the formula

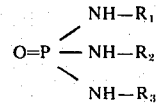

wherein $R_1$, $R_2$ and $R_3$ are selected from straight or branched chain alkyl radicals of from 10 to 24 carbon atoms each, having properties such that, when added in small amounts to strong acid alkylation catalysts, increased yields of high quality products and lower consumption of alkylation catalyst are experienced. Additionally, the efficiency of the alkylation reaction is increased such that lower ratios of isoparaffin to olefin may be employed.

Compounds of the present invention useful as alkylation aids are NN'N'' tris (alkyl) phosphoric triamides having relatively long chain alkyl radicals attached to each of the nitrogen atoms. Such alkyl radicals may have from 10 to 24 carbon atoms and may be either straight or branched chain. Preferably, the alkyl radicals are from 12 to 20 carbon atoms in length and particularly preferred is a straight chain alkyl radical of 18 carbon atoms (the octadecyl radical). Generally, in a given NN'N'' tris (alkyl) phosphoric triamide, variations in the carbon number of the alkyl radicals in a particular molecule will not be great. However, alkyl radicals of various carbon numbers, including normal and branched chain isomers, may be incorporated in a single molecule. Desirably, the total alkyl carbons in a molecule of the NN'N'' tris (alkyl) phosphoric triamide will be in the range of 30 to 72. The amount of NN'N'' tris (alkyl) phosphoric triamide compounds of the present invention which are employed in an alkylation reaction may be varied from about 0.0005 to about 0.5 weight percent of the strong acid catalyst phase employed. At concentrations below about 0.0005, the benefits obtained from such triamides is not substantial. At concentrations above about 0.5 weight percent, surface active characteristics become prevalent and emulsions of hydrocarbon reactant and catalyst phase may become difficult to separate.

The present invention is applicable to alkylation reactions, that is reaction of an alkylatable hydrocarbon with an alkylation agent. Alkylatable hydrocarbons within the meaning of the present invention include isoparaffin hydrocarbons, aromatic hydrocarbons, cycloparaffin hydrocarbons, etc. Alkylating agents include compounds such as olefins, alcohols, alkyl esters, ethers, alkyl sulfates, and others capable of contributing an alkyl radical to form a 1:1 adduct with an alkylatable hydrocarbon under alkylation reaction conditions. Particularly, the present invention is applicable to alkylation of isoparaffin hydrocarbons of from 4 to 6 carbon atoms, and preferably isobutane, with olefin hydrocarbons of from 3 to 5 carbon atoms, preferably propylene, butylenes, or mixtures thereof.

Olefin hydrocarbons are highly reactive under alkylation conditions and sufficient alkylatable hydrocarbon is provided to react with essentially all the olefins present. Preferably, a substantial excess of alkylatable hydrocarbons, is provided to ensure more complete reaction of olefins with the alkylatable hydrocarbons. Molar ratios of isoparaffin to olefin may range from about 1/1 to about 50/1, and molar ratios of about 5/1 to about 20/1 are preferred. Many anomalous side reactions occur in alkylation reactions resulting in formation of paraffin hydrocarbons of low octane number and in formation of acid sludges which limit the life of the acid catalyst. Commonly, high isoparaffin to olefin molar ratios in the range of 20/1 to 50/1 have been maintained in alkylation reactions to maximize reaction selectivity to the desired highly branched alkylate products. Such high isoparaffin to olefin ratios add expense to the process, since excess isoparaffin must be fractionated or otherwise separated from the alkylate hydrocarbon product, and additional reaction zone volume must be provided. Unexpectedly we have discovered that small amounts of NN'N'' tris (alkyl) phosphoric triamides added to the acid catalyst substantially improves selectivity of the alkylation reaction for formation of the desired highly branched alkylate hydrocarbons. This increased reaction efficiency employing the alkylation aids of the present invention allows lowering of the isoparaffin to olefin molar ratio without deletereous effect on alkylate product quality. Additionally, with use of the disclosed alkylation aids, increased amounts of olefin hydrocarbon may be reacted in an alkylation process of given reaction zone volume.

In alkylation reaction contemplated in the present invention, reactants are maintained in the liquid phase. Reactants are not necessarily normally liquid, and superatmospheric reaction pressures are employed to maintain such liquid phase. Reaction pressures of from about 10 to 150 psig are preferred, although higher and lower pressures may be used without adverse effect so long as reactants remain in the liquid phase.

Catalysts for alkylation reactions include strong Bronsted and Lewis acids such as, for example, HF, $H_2SO_4$, fluorosulfonic, mixtures of $H_2SO_4$ and fluorosulfonic, aluminum chloride, etc. Acid catalysts which form heterogeneous liquid phases in the presence of liquid reactants are contemplated in the present invention. While various strong acid catalysts can be used, strong acid catalysts comprising about 88–98 weight percent $H_2SO_4$ are particularly preferred. When such sulfuric acid catalyst is used, reaction temperatures may range from below 0° to about 150°F. At lower temperatures, reaction rates are slower including side reaction rates which contribute undesirable side products, and at higher temperatures reaction rates increase, particularly the undesirable self-polymerization of olefins. Preferred reaction temperature for alkylation reactions of isoparaffins with olefins in the presence of sulfuric acid catalyst are in the range of 0°–100°F. and especially preferred are temperatures in the range of 20°–75°F.

Olefin hydrocarbons, in the presence of acid catalysts, tend to self-polymerize into relatively high molecular weight polymers. The polymers then tend to crack into lower molecular weight hydrocarbons. The polymers and cracked hydrocarbons represent lost yield of desired alkylate product. Also in isoparaffin-olefin alkylation reactions for production of high octane alkylate, olefin polymers and cracked hydrocarbons are particularly undesirable as they are of low octane value and possess a substantial degree of unsaturation. Olefin polymers are difficult to separate from liquid strong acid alkylation catalyst, thus contributing to a decrease in acid strength of such catalyst. Decreased acid strength adversely effects the alkylation reaction, lowering the alkylation reaction rate and increasing formation of less desirable alkylate isomers. Also, reactions occur with the acid to form acid-oils. Consequently, acid is consumed in alkylation reactions in which polymerization and cracking occur as side reactions. In commercial practice, a portion of used catalyst is withdrawn from the alkylation system and replaced with fresh concentrated acid in order to maintain alkylation catalyst at a selected acid concentration. The withdrawn acid, known as spent acid, must then be regenerated or disposed of at considerable expense.

Commonly, commercial alkylation processes are continuous flow operations, although batch operations may also be performed. In a continuous flow process, reactant hydrocarbons and acid catalyst are contacted with agitation in a reaction zone. Reaction zone effluent is separated into a hydrocarbon phase and an acid phase with a portion of the separated acid phase being recycled for contact with additional reactants. If desired, a plurality of alkylation zones may be arranged to receive serial flow of acid phase and/or reactant phase. The isoparaffin is preferably present in substantial excess to olefin reactant, and an isoparaffin stream may be introduced as a liquid or as a gas, and may enter the reaction zone with the isoparaffin, the acid, or may be introduced separately into the reaction mixture present in the reaction zone.

The alkylation reaction effluent hydrocarbon phase comprises isoparaffin hydrocarbon and contains a substantial amount of alkylate hydrocarbon product. The alkylate hydrocarbon is separated from the isoparaffin in an alkylate recovery section, which may comprise one or more fractional distillation zones and/or other separation means. Preferably, in a commercial process, isoparaffin hydrocarbon separated from the reaction effluent is recycled as reactant to an alkylation reaction zone.

The use of the NN'N'' tris (alkyl) phosphoric triamides disclosed in the present application as alkylation catalyst aids, particularly in sulfuric acid catalyzed alkylation of isoparaffins with olefins, improves yield and quality of product alkylate. The alkylation reaction is promoted, thus additional amounts of isoparaffin-olefin alkylate hydrocarbon is produced and, concomitantly, less olefin polymer and resulting cracked products are produced. Additionally, the formation of highly branched alkylate hydrocarbons is favored over their less highly branched isomers. In production of gasoline range alkylate, highly branched isomers are preferred since octane number increases with increased branching. With reduction in polymer and cracked hydrocarbon formation, acid consumption is also substantially decreased. In order to clearly demonstrate these advantages of the disclosed NN'N'' tris (alkyl) phosphoric triamides in alkylation reactions, the following specific examples are included. These examples, disclosing specific embodiments of the present invention, are included for the purpose of demonstrating the invention. These examples are not presented in a limiting sense and are not intended to restrict the scope of the invention.

EXAMPLE I

In this example an NN'N'' tris (n-octadecyl) phosphoric triamide having the following chemical formula was prepared:

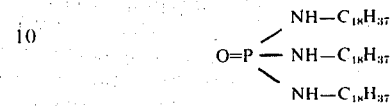

80.7 g. (0.3 mol) of Armeen 18D (technical grade of n-octadecyl amine) were charged to a 3-necked flask equipped with a stirrer and a Dean-Stark trap, along with 200 ml. of benzene and 30.3 g. (0.3 mol) triethylamine. The solution was heated to 70°C. and 15.3 g. (0.1 mol) $POCl_3$ were added over a period of 30 minutes, during which time the temperature rose to 82°C. The reaction mixture was heated for an additional hour at 82°C. Then 200 ml $H_2O$ were added and the mixture heated with stirring to 72°C. Stirring was stopped and the water layer was allowed to separate. As much $H_2O$ layer as possible was siphoned off and the remainder (about 40 ml) was removed as a benzene-water azeotrope. The solution in the flask was filtered while hot and allowed to cool to room temperature over 16 hours. The resulting white precipitate was washed with benzene and dried. Yield was 72 g. (83.7%) white crystals melting at 85°–88°C. and containing 3.71% P (theory 3.65%) and 4.5% N (theory 4.95%).

The product NN'N'' tris (octadecyl) phosphoric triamide was dissolved in concentrated sulfuric acid to form a solution comprising one (1) part NN'N'' tris (octadecyl) phosphoric triamide and nine (9) parts $H_2SO_4$. This solution was used in the following examples to add the disclosed alkylation aid to the alkylation reactions.

EXAMPLE II

In this example, NN'N'' tris (n-octadecyl) phosphoric triamide, prepared in Example I was added to a sulfuric acid alkylation catalyst. The sulfuric acid catalyst employed comprised catalyst from a commercial alkylation process refortified with fresh, concentrated $H_2SO_4$. Separate alkylation runs were made, two using sulfuric acid catalyst treated with NN'N'' tris (n-octadecyl) phosphoric triamide and the other using untreated sulfuric acid catalyst. In these alkylation runs, isobutane was alkylated with butene-2 and operating conditions and results are shown in Table I, below.

TABLE I

| Run No. | 1 | 2 | 3 |
|---|---|---|---|
| Catalyst | 95.2 % $H_2SO_4$ | 95.2 % $H_2SO_4$ | 95.2 % $H_2SO_4$ |
| N,N',N'' tris (n-octadecyl) phosphoric triamide (wt. % catalyst) | 0 | 0.011 | 0.011 |
| Isobutane: butene-2 weight ratio | 6:1 | 6:1 | 6:1 |
| Alkylation Reaction Temperatures (°F.) | 49 | 50 | 47 |
| Butene-2 space velocity (Vol. olefin/hr./vol. catalyst) | 0.2 | 0.2 | 0.2 |
| Alkylate Composition | | | |
| $C_5$ | 2.1 | 2.6 | 1.9 |
| $C_6$ | 5.3 | 5.1 | 4.2 |
| $C_7$ | 5.0 | 4.9 | 4.1 |
| $C_8$ | 66.5 | 72.2 | 73.3 |
| $C_9$ | 21.2 | 14.8 | 16.5 |
| Trimethyl Pentane (wt.% of alkylate) | 51.9 | 61.5 | 64.5 |
| Alkylate Research Octane Number (clear) | 92.6 | 93.9 | 95.2 |

TABLE I-continued

| Run No. | 1 | 2 | 3 |
|---|---|---|---|
| Alkylate Motor Octane Number (clear) | 89.8 | 90.7 | 91.8 |

From an examination of the results reported in Table I above, it can be seen that an isobutane-butene-2 alkylation reaction employing a small amount (0.011 wt.%) NN′N″ tris (n-octadecyl) phosphoric triamide produces alkylate of substantially higher octane for use in a motor fuel blend than an alkylate produced under similar conditions using untreated sulfuric acid catalyst. That is, the alkylate produced using catalyst treated with the alkylation aid of the present invention has a substantially increased research octane number (95.2 vs. 92.6) and has substantially increased $C_8$ hydrocarbon content (73.3% vs. 66.5%) over alkylate produced using catalyst without the additive. In addition, the concentration of desirable trimethyl pentanes in the alkylate product is substantially increased (64.5% vs. 51.9%) for alkylate produced according to the method of the present invention.

EXAMPLE III

In this example mixed olefin feed composed of 60 parts butene-2 and 40 parts propene was employed to alkylate isobutane. Sulfuric acid catalyst for the alkylation reaction was spent acid from a commercial alkylation process refortified with fresh, concentrated $H_2SO_4$. Three separate alkylation runs were made: Run 4 was a comparison run wherein no alkylation aid was used; Run 5 employed 0.0055 wt.% NN′N″ tris (octadecyl) phosphoric triamide in the acid catalyst; and Run 6 employed 0.011 wt.% NN′N″ tris (octadecyl) phosphoric triamide in the acid catalyst. Operating conditions and results of Runs 4–6 are shown in Table II below.

From an examination of the results reported in Table II above, it can be seen that addition of a small amount (0.0055 wt. %) of the disclosed alkylation aid in Run 5 improved alkylate octane substantially over alkylate octanes obtained in Run 4 without the alkylation aid. Additionally, the percent of trimethyl pentane increased substantially in the alkylate produced with alkylation aid, and the amount of $C_9^+$ heavy alkylate decreased substantially. In Run 6, where the alkylation aid was increased to 0.011 wt.%, further increase in alkylate octane values was obtained as well as an increase in the amount of trimethyl pentane in the alkylate product.

We claim:

1. An alkylation catalyst consisting essentially of concentrated sulfuric acid having a concentration from about 88 to about 98 weight percent $H_2SO_4$ and containing from about 0.0005 to about 0.5 weight percent of a NN′N″ tris (alkyl) phosphoric triamide having the formula:

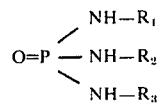

wherein $R_1$, $R_2$, and $R_3$ are selected from the group consisting of straight chain and branched chain alkyl radicals each having from 10 to 24 carbon atoms.

2. The alkylation catalyst of claim 1 wherein $R_1$, $R_2$ and $R_3$ are octadecyl alkyl radicals.

* * * * *

TABLE II

| Run No. | 4 | 5 | 6 |
|---|---|---|---|
| Catalyst (wt.% $H_2SO_4$) | 95.2 | 95.2 | 95.2 |
| N,N′,N″ tris (n-octadecyl) phosphoric triamide (wt.% of catalyst) | 0 | 0.0055 | 0.011 |
| Isobutane: Olefin wt. ratio | 5.45/1 | 5.45/1 | 5.45/1 |
| Alkylation Temperature (°F.) | 46 | 47 | 46 |
| Olefin space velocity (vol. olefin/hr/vol. catalyst) | 0.2 | 0.2 | 0.2 |
| Spent Alkylation Acid (wt.% $H_2SO_4$) | 93.4 | 95.0 | — |
| Alkylate Composition (alkylate wt.%) | | | |
| $C_5$ | 1.8 | 1.3 | 0.6 |
| $C_6$ | 4.4 | 3.5 | 2.5 |
| $C_7$ | 9.6 | 10.4 | 8.6 |
| $C_8$ | 66.4 | 72.3 | 76.8 |
| $C_9^+$ | 17.8 | 12.4 | 11.4 |
| Alkylate Bromine No. | 2.6 | 0.6 | 1.8 |
| Trimethyl pentanes (wt.% of alkylate) | 56.6 | 65.8 | 70.4 |
| Dimethyl pentanes (wt.% of alkylate) | 9.3 | 10.1 | 8.4 |
| Research Octane (clear) | 94.0 | 96.3 | 96.9 |
| Motor Octane (clear) | 90.9 | 92.8 | 93.3 |